United States Patent
Azizova et al.

(10) Patent No.: US 7,527,653 B2
(45) Date of Patent: May 5, 2009

(54) HAIR COLORING COMPOSITION

(75) Inventors: Marina Azizova, New Canaan, CT (US); Yanping Zhou, River Edge, NJ (US); Rushi Tasker, Trumbull, CT (US)

(73) Assignee: Zotos International, Inc., Darien, CT (US)

( * ) Notice: Subject to any disclaimer, the term of this patent is extended or adjusted under 35 U.S.C. 154(b) by 0 days.

(21) Appl. No.: 11/804,270

(22) Filed: May 17, 2007

(65) Prior Publication Data

US 2007/0277330 A1    Dec. 6, 2007

Related U.S. Application Data

(60) Provisional application No. 60/811,644, filed on Jun. 6, 2006.

(51) Int. Cl.
*A61Q 5/10* (2006.01)
(52) U.S. Cl. .................... 8/405; 8/406; 8/435; 8/565; 8/567
(58) Field of Classification Search ............... 8/405, 8/406, 435, 565, 567
See application file for complete search history.

(56) References Cited

U.S. PATENT DOCUMENTS

| | | | |
|---|---|---|---|
| 4,129,413 | A | 12/1978 | Rose et al. |
| 4,396,392 | A | 8/1983 | Konrad et al. |
| 4,552,565 | A | 11/1985 | Maak et al. |
| 4,838,893 | A | 6/1989 | Rose et al. |
| 4,900,325 | A | 2/1990 | Rose et al. |
| 5,089,257 | A | 2/1992 | Schrader et al. |
| 5,230,710 | A | 7/1993 | Akram et al. |
| 5,334,225 | A | 8/1994 | Ogawa et al. |
| 6,743,263 | B1 | 6/2004 | Hoeffkes et al. |
| 6,750,355 | B2 | 6/2004 | Lim et al. |
| 2004/0255402 | A1* | 12/2004 | Knuebel et al. ........ 8/405 |

* cited by examiner

*Primary Examiner*—Eisa B Elhilo
(74) *Attorney, Agent, or Firm*—Melvin I. Stoltz

(57) ABSTRACT

By providing a certain oxidative primary and a certain oxidative coupler as an integral ingredients in hair coloring formulations, substantially improved and enhanced hair conditioning benefits are attained, providing a highly effective, hair coloring composition.

11 Claims, No Drawings

HAIR COLORING COMPOSITION

RELATED APPLICATIONS

This application relates to U.S. Provisional Patent Application Ser. No. 60/811,644, filed Jun. 6, 2006 for a Hair Coloring Composition.

TECHNICAL FIELD

This invention relates to hair coloring compositions and, more particularly, to hair coloring compositions which provide vibrant colors to the hair fibers.

BACKGROUND ART

Throughout the years, there has been a desire to alter the color of synthetic and natural fibers. In particular, coloring of human hair has been sought in view of changing styles and fashion. However, due to the inherent composition of hair fiber, and the chemical and mechanical exposure encountered by the hair fibers during normal care and styling, obtaining and maintaining a precise color has been an illusive goal.

As is well known, hair is composed of a unique protein material called "keratin" which is repeatedly being subjected to both chemical and mechanical damage from combing and brushing, as well as from sunlight, chlorinated water, shampooing, permanent waving, and other such treatments involving various chemicals. As a result, depending upon the length of the hair fibre, the distal ends of each hair fiber tend to have substantially more damage than the proximal ends nearer to the scalp. This inconsistency causes variation in the dye uptake by the hair fiber, resulting in color variations along the length of the hair fiber.

In spite of the long history with the coloration of hair and the extensive effort that has been expended in attempting to eliminate the problems associated with the dyeing of human hair, no system has been achieved which is capable of overcoming all of the drawbacks and difficulties encountered with hair dyes.

Other problems which continue to plague conventional prior art dyes are the longevity or wearability of the resulting color, its ability to resist fading, and its ability to resist changes due to washing, combing, or rubbing. Furthermore, the accuracy of the color imparted to the hair fiber during the dyeing process, as well as the ease with which the hair fiber is capable of being dyes, are also important factors which prior art dye compositions have been incapable of successfully overcoming. New inventions and novel combinations of hair dyes create progress in the art of hair color and increase consumer satisfaction with hair coloring products.

In general, prior art hair coloring and fiber coloring mixtures comprise dyestuffs obtained from coal tar derivatives or from synthetic routes. These mixtures are typically formulated to provide a particularly desired wearability of the color on the fiber. Dyes formulated for coloring hair fibers, are typically termed temporary, semi-permanent, demi-permanent, or permanent.

Temporary and semi-permanent dyes or hair colors last through a few shampooings, while demi-permanent and permanent hair colors are retained for six weeks and longer.

Temporary and semi-permanent hair coloring compositions typically comprise mixtures of one or several dyestuffs in a solution containing solvents and water. Often the hair coloring is employed in a lotion or a foam base which allows the product to be applied in various "shampoo-in" applications.

The amount of color deposited by temporary and semi-permanent hair coloring compositions is subject to substantial variations, although the actual color deposited is typically low. In addition, grey hair is the most difficult to color in this way and loses the applied color most rapidly upon shampooing. As a result, repeated re-applications are necessary.

If an individual does not regularly have the color reapplied, the hair fibers will develop an uneven hair color, due to an uneven distribution of the dye along the hair fibers. This produces an unnatural appearance and cast to the hair. Furthermore, the repeated use required by such product causes the excess dyestuff rinsed from the hair to enter the waterways, thereby adding to the cumulative problems presently being realized in the contamination of ground water.

In view of the difficulties and drawbacks detailed above in regard to semi-permanent hair colors and temporary hair colors, individuals wishing to dye their hair have sought the use of permanent dye formulations. In particular, professional hair stylists prefer the use of permanent dye formulations, since they wish to provide their customers with more durable and longer lasting results.

In using virtually all prior art permanent hair dyes, hydrogen peroxide is required along with the particular dyestuffs. During the application, the mixture enters into the hair fibers and reacts therein to form larger dyes of a predetermined color. Since the dye molecules formed inside the fiber are larger than the molecules entering the hair fibers, the formed dyes are trapped within the hair fibers, and are unable to easily diffuse out of the fibers. Consequently, the resulting coloring is trapped within the hair fiber and is virtually permanent.

One advantage that has been found from using these types of dye mixtures is the ability to lighten hair, since the presence of both hydrogen peroxide and the alkaline environment of the mixture will also remove natural hair color, which is then replaced by the colors formed in situ.

One principal concern that has existed in the prior art is that the typical processes used to color hair involve contacting the hair with a mixture of dyes and ammonia and hydrogen peroxide. This combination can cause irreversible damage to the keratin matrix of the hair fiber. Furthermore, in order to be effective, the process requires some mode of swelling of the hair to allow for the penetration of the dye. In the case of tint impartation, whereby the deposited color is a shade or tone lighter than the naturally underlying color, a bleaching of the natural color is required.

Due to the attention that has been given to hair dyeing, the mechanisms involved in the action of the dye formation are well understood. In addition, the damage done to the hair fibers is also well-known. In particular, some characteristics of this damage are the dimmunization of the structural integrity of the hair fibers, as evidenced by the loss of resiliency and increased-porosity or capability to uptake water.

As is apparent from the preceding discussion, numerous attempts and extensive effort has been expended through the long history of dye use to achieve a commercially successful dye product. However, no such product has been attained which is capable of providing a universally applicable, commercially acceptable product which overcomes all of the known drawbacks. In addition, the prior art dye systems have often proven to be expensive, while providing only limited or partial success.

Therefore, it is a principal object of the present invention to provide a permanent or long lasting dye composition for use on human hair which is capable of being easily and successfully employed on all desired hair fibers with consistent, repeatable and predictable coloration results.

Another object of the present invention is to provide a permanent dye composition having the characteristic features described above which is long lasting, durable and incapable of being washed from the fibers.

Other and more specific objects will in part be obvious and will in part appear hereinafter.

DETAILED DESCRIPTION

By employing the present invention, the prior art failings and drawbacks have essentially been overcome, and a highly effective, hair coloring compositions is obtained which also provides vibrant colors to the hair fibers. It has been found that the color depth achieved by the present invention is substantially greater than any prior art formulation.

In accordance with the present invention, it has been found that by combining a specific oxidative primary with a specific oxidative coupler, a unique, unpredictable, and synergistic result is obtained. In this invention, it has been discovered that by combining 2,4,5,6-tetraaminopyrimidine sulfate with 2,6-bis(2-hydroxyethylamino)toluene in a hair coloring composition, an extremely vibrant red color is attained.

Although these two dye ingredients are found in prior art hair coloring compositions, no prior art reference has ever suggested the combination of these ingredients in a single formulation. Furthermore, nothing in the prior art teaching regarding these two ingredients provides any suggestion of the synergistic interaction achieved by the present invention. As a result, no one skilled in this art could have predicted the deep, vibrant red color which is attained by the combination of the present invention.

In accordance with the present invention, it has been found that whenever 2,4,5,6-tetraaminopyrimidine sulfate is coupled with 2,6-bis(2-hydroxyethylamino)toluene in the presence of hydrogen peroxide, an unexpected and unpredictable vibrant red color is achieved. Furthermore, it has been found that the vibrant red color which is attained by combining 2,4,5,6-tetraamino-pyrimidine sulfate with 2,6-bis(2-hydroxyethylamino)toluene in the presence of hydrogen peroxide is substantially greater and more vibrant than any red color attained by employing either of these dyes alone or in combination with other common hair dyes available in the prior art.

Although other dye formulations may be incorporated in an overall hair composition for coloring human hair, the present invention is specifically limited to the combination of 2,4,5,6-tetraaminopyrimidine sulfate with 2,6-bis(2-hydroxyethylamino)toluene in a hair coloring composition for producing the unexpected and unanticipated vibrant red color. Furthermore, the combination of the present invention employs 2,4,5,6-tetraaminopyrimidine sulfate as an oxidative primary and 2,6-bis(2-hydroxyethylamino)toluene as an oxidative coupler, which are combined in the presence of hydrogen peroxide. When employed in this manner, a unique, unpredictable, synergistic interaction occurs which provides an unexpected vibrant red coloring to the hair fibers. As a result, hair coloring previously unattainable is now realized using the combination of dyes and the teaching of the present invention.

In addition, it has also been found that optimum results are realized by employing a concentration of between about 0.001 and 5.0% by weight based by the weight of the entire composition of 2,4,5,6-tetraaminopyrimidine sulfate and 2,6-bis(2-hydroxyethylamino)toluene. The remainder of the composition comprises other dyes which may be desired, along with additional ingredients known in the art for producing a final composition which can be applied to the hair fibers as a one selected from the group consisting of powdered mixtures, cream emulsions, liquids, and gels.

In addition, it has also been found that hair coloration is preferably carried out using hydrogen peroxide as the oxidizing agent. In this regard, a 6% solution of hydrogen peroxide is preferably employed and intermixed with the dye composition at a ratio of 1:1.

BEST MODE FOR CARRYING OUT THE INVENTION

In order to demonstrate the efficacy of the present invention and the achievement of a hair dye or hair coloring composition which provide a vibrant red coloring to the hair fibers, a plurality of alternate compositions were manufactured in accordance with the present invention and tested as detailed below. The following Examples are presented in order to fully demonstrate the highly effective hair dye and hair coloring compositions of the present invention and the substantially enhanced results achieved thereby.

By reviewing the following Examples, the ability of the hair dye or hair coloring compositions of the present invention to provide the desired results is clearly established. However, it is to be understood that the following Examples are intended as a teaching of the best mode for carrying out the present invention and are not intended to limit the breadth of this discovery.

EXAMPLES

In Table 1, numerous alternate hair dying formulations are fully detailed, each of which were separately prepared and tested. Each formulation was made in the form of a hair dyeing cream emulsion, with the specific combination of ingredients for each formulation being fully detailed in Table 1.

TABLE 1

| Component | 1 | 2 | 3 | 4 | 5 | 6 | 7 | 8 | 9 | 10 | 11 |
|---|---|---|---|---|---|---|---|---|---|---|---|
| | | | | | | % by Weight | | | | | |
| cetyl alcohol | 4.50 | 4.50 | 4.50 | 4.50 | 4.50 | 4.50 | 4.50 | 4.50 | 4.50 | 4.50 | 4.50 |
| Stearic acid | 2.00 | 2.00 | 2.00 | 2.00 | 2.00 | 2.00 | 2.00 | 2.00 | 2.00 | 2.00 | 2.00 |
| glyceryl stearate | 2.00 | 2.00 | 2.00 | 2.00 | 2.00 | 2.00 | 2.00 | 2.00 | 2.00 | 2.00 | 2.00 |
| steareth-21 | 2.00 | 2.00 | 2.00 | 2.00 | 2.00 | 2.00 | 2.00 | 2.00 | 2.00 | 2.00 | 2.00 |
| cetearyl alcohol | 1.50 | 1.50 | 1.50 | 1.50 | 1.50 | 1.50 | 1.50 | 1.50 | 1.50 | 1.50 | 1.50 |
| glycol distearate | 1.00 | 1.00 | 1.00 | 1.00 | 1.00 | 1.00 | 1.00 | 1.00 | 1.00 | 1.00 | 1.00 |
| stearamidopropyl dimethylamine | 1.50 | 1.50 | 1.50 | 1.50 | 1.50 | 1.50 | 1.50 | 1.50 | 1.50 | 1.50 | 1.50 |
| mineral oil | 1.50 | 1.50 | 1.50 | 1.50 | 1.50 | 1.50 | 1.50 | 1.50 | 1.50 | 1.50 | 1.50 |
| isostearic acid | 0.75 | 0.75 | 0.75 | 0.75 | 0.75 | 0.75 | 0.75 | 0.75 | 0.75 | 0.75 | 0.75 |
| oleyl alcohol | 2.00 | 2.00 | 2.00 | 2.00 | 2.00 | 2.00 | 2.00 | 2.00 | 2.00 | 2.00 | 2.00 |

TABLE 1-continued

| Component | 1 | 2 | 3 | 4 | 5 | 6 | 7 | 8 | 9 | 10 | 11 |
|---|---|---|---|---|---|---|---|---|---|---|---|
| | | | | | | % by Weight | | | | | |
| C12-15 alkyl benzoate | 2.00 | 2.00 | 2.00 | 2.00 | 2.00 | 2.00 | 2.00 | 2.00 | 2.00 | 2.00 | 2.00 |
| propylene glycol | 4.50 | 4.50 | 4.50 | 4.50 | 4.50 | 4.50 | 4.50 | 4.50 | 4.50 | 4.50 | 4.50 |
| erythorbic acid | 0.40 | 0.40 | 0.40 | 0.40 | 0.40 | 0.40 | 0.40 | 0.40 | 0.40 | 0.40 | 0.40 |
| EDTA | 0.10 | 0.10 | 0.10 | 0.10 | 0.10 | 0.10 | 0.10 | 0.10 | 0.10 | 0.10 | 0.10 |
| sodium sulfite | 0.10 | 0.10 | 0.10 | 0.10 | 0.10 | 0.10 | 0.10 | 0.10 | 0.10 | 0.10 | 0.10 |
| phosphoric acid | 0.98 | 0.98 | 0.98 | 0.98 | 0.98 | 0.98 | 0.98 | 0.98 | 0.98 | 0.98 | 0.98 |
| 2,4,5,6-tetraaminopyrimidinesulfate | 0.60 | 0.80 | 1.20 | | | | | 1.20 | 1.20 | 1.20 | 1.20 |
| 2,6-bis(2-hydroxyethylamino)toulene | 0.53 | 0.70 | 1.05 | 1.05 | 1.05 | 1.05 | 1.05 | | | | |
| p-phenylenediamine | | | | 0.55 | | | | | | | |
| p-aminophenol | | | | | 0.55 | | | | | | |
| 4-amino-m-cresol | | | | | | 0.62 | | | | | |
| n,n-bis(2-hydroxyethyl)-p-phenylenediamine sulfate | | | | | | | 1.57 | | | | |
| resorcinol | | | | | | | | 0.55 | | | |
| m-aminophenol | | | | | | | | | 0.55 | | |
| 2-methylresorcinol | | | | | | | | | | 0.62 | |
| 2,4-diaminophenoxyethanol HCl | | | | | | | | | | | 1.20 |
| water | | | | | | Add to 100 | | | | | |
| Color Results | Light Red | Red | Vibrant Intense Red | Cool Purple | Cool Magenta | Pale Violet | Vibrant Purple | Reddish Brown | Dull Violet | Orange | Blue-Green |

In formulating each composition detailed in Table 1, the individual ingredients were mixed together at 75-80° C. and, after cooling, were adjusted to a pH of 9.5-10.0 using NH$_4$OH. Furthermore, in testing each of the formulations, coloration was carried out using hydrogen peroxide as the oxidizing agent.

In order to achieve the desired oxidative development of the coloration, each of the compositions in Table 1 were mixed with 6% strength hydrogen peroxide in the ratio of 1:1. Each formulation was applied to approximately 10 cm long tresses of 100% gray human hair which had not been pre-treated in any way. Each hair dye composition was allowed to remain on the hair for 35 minutes at 25° C. When the dyeing process was complete, the hair fibers were rinsed, washed with a customary shampoo and then dried. The coloring results are detailed in Table 1.

As clearly shown in Table 1, the dyeing results achieved using the formulations defined in Examples 1, 2, and 3 unequivocally demonstrate that the use of 2,4,5,6-tetraaminopyrimidinesulfate coupled with 2,6-bis(2-hydroxyethylamino)toluene produced an unexpected vibrant red color that is incapable of being achieved by employing either of these dyes individually or with other common hair dyes available in the art. The dyeing results from the formulations of Examples 4-7 show that other oxidative primary dyes such as p-phenylenediamine, p-aminophenol, 4-amino-m-cresol and n,n-bis(2-hydroxyethyl)-p-phenylenediamine sulfate when coupled with 2,6-bis(2-hydroxyethylamino)toluene produced undesirable coloring results ranging between cool purple, cool magenta, pale violet and vibrant purple. In addition, the dyeing results produced from the formulation of Examples 8-11 show that 2,4,5,6-tetraaminopyrimidine sulfate coupled with other oxidative couplers like resorcinol, m-aminophenol, 2-methylresorcinol and 2,4-diaminophenoxyethanol HCl produced undesirable reddish brown, dull violet, orange and blue and green coloring which are not suitable for common or fashion hair color shades.

It will thus be seen that the objects set forth above, among those made apparent from the preceding description, are efficiently attained and, since certain changes may be made in carrying out the above process without departing from the scope of the invention, is intended that all matter contained in the above description shall be interpreted as illustrative and not in a limiting sense.

It is also to be understood that the following claims are intended to cover all of the generic and specific features of the invention herein described, and all statements of the scope of the invention which, in an matter of language, might be said to fall therebetween.

Particularly, it is to be understood that in said claims, ingredients or compounds recited in the singular are intended to include compatible mixtures of such ingredients whenever the sense permits.

Having described our invention what we claim as new and desire to secure by Letters Patent is:

1. A composition for coloring keratinaceous fibers with a vivid red color comprising a combination of 2,4,5,6-tetraaminopyrimidine sulfate and 2,6-bis(2-hydroxyethylamino)toluene with both dyes having a total combined concentration ranging between about 1.10% and 5.0% by weight based upon the weight of the entire composition.

2. The composition defined in claim 1, wherein the 2,4,5,6-tetraaminopyrimidine sulfate dye is employed as an oxidative primary and the 2,6-bis(2-hydroxyethylamino)toluene is employed as an oxidative coupler.

3. The composition defined in claim 1, wherein the 2,4,5,6-tetraaminopyrimidine sulfate is coupled with 2,6-bis(2-hydroxy-ethylamino)toluene in the presence of hydrogen peroxide to produce a vibrant red color and are the only hair dye ingredients in the entire formulation.

4. The composition defined in claim 1, wherein other hair dyes are incorporated into the overall composition.

5. The composition defined in claim 1, wherein the composition is formulated as one selected from the group consisting of powder mixtures, cream emulsions, gels, and liquids.

6. A method for coloring keratin fibers comprising the steps of:

A. mixing 2,4,5,6-tetraaminopyrimidine sulfate and 2,6-bis(2-hydroxyethylamino)toluene in a hair application carrier to produce a hair dyeing composition having a total combined concentration ranging between about 1.10% and 5.0% by weight based upon the weight of the entire composition, B. adding hydrogen peroxide to the hair dyeing composition as an oxidizing agent, and C. applying the fully intermixed composition to hair fibers for producing a vibrant red color thereto.

7. The method defined in claim 6, wherein the hydrogen peroxide comprises a 0% to 12% strength and is combined with the hair dyeing composition in a 1:1 ratio.

8. The method defined in claim 7, wherein the 2,4,5,6-tetraaminopyrimidine sulfate and the 2,6-bis(2-hydroxyethylamino)toluene are mixed into the hair application carrier as the only hair dye ingredients therein.

9. The method defined in claim 8, wherein the hair application carrier comprises a cream emulsion.

10. The method defined in claim 6, and comprising the additional steps of:

D. mixing the individual constituents together at a temperature ranging between about 75 and 80° C.;

E. allowing the composition to cool; and

F. adjusting the pH to between about 9.5 and 10 using NH4OH.

11. The method defined in claim 10, comprising the additional steps of:

G. applying the hair dyeing composition to the hair fibers for 35 minutes at a temperature of 25° C.;

H. rinsing the dyeing composition from the hair fibers;

I. washing the treated hair with a shampoo; and

J. drying the dye hair fibers.

* * * * *